(12) United States Patent
Gupta

(10) Patent No.: US 6,958,319 B2
(45) Date of Patent: *Oct. 25, 2005

(54) FORMULATION OF BORONIC ACID COMPOUNDS

(75) Inventor: Shanker Lal Gupta, Rockville, MD (US)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 79 days.

This patent is subject to a terminal disclaimer.

(21) Appl. No.: 10/664,732

(22) Filed: Sep. 18, 2003

(65) Prior Publication Data

US 2004/0063623 A1 Apr. 1, 2004

Related U.S. Application Data

(63) Continuation of application No. 10/056,567, filed on Jan. 25, 2002, now Pat. No. 6,713,446, and a continuation of application No. 10/056,563, filed on Jan. 25, 2002, now Pat. No. 6,699,835.
(60) Provisional application No. 60/264,160, filed on Jan. 25, 2001.

(51) Int. Cl.$^7$ .................... A61K 38/00; A61K 33/22; C07K 9/00; C07F 5/02
(52) U.S. Cl. .............. 514/2; 514/18; 514/19; 514/64; 536/17.1; 544/229; 530/322
(58) Field of Search ................... 514/2, 18, 19, 514/64; 536/17.1; 544/229; 530/322

(56) References Cited

U.S. PATENT DOCUMENTS

| | | | |
|---|---|---|---|
| 4,499,082 A | 2/1985 | Shenvi et al. | |
| 5,106,948 A | 4/1992 | Kinder et al. | |
| 5,169,841 A | 12/1992 | Kleeman et al. | |
| 5,187,157 A | 2/1993 | Kettner et al. | |
| 5,242,904 A | 9/1993 | Kettner et al. | |
| 5,250,720 A | 10/1993 | Kettner et al. | |
| 5,492,900 A | 2/1996 | LaHann | |
| 5,574,017 A | 11/1996 | Gutheil | |
| 5,780,454 A | 7/1998 | Adams et al. | |
| 5,935,944 A | 8/1999 | LaHann | |
| 5,990,083 A | 11/1999 | Iqbal et al. | |
| 6,066,730 A | 5/2000 | Adams et al. | |
| 6,083,903 A | 7/2000 | Adams et al. | |
| 6,169,076 B1 | 1/2001 | Shull et al. | |
| 6,297,217 B1 | 10/2001 | Adams et al. | |
| 6,699,835 B2 * | 3/2004 | Plamondon et al. | 514/2 |
| 6,713,446 B2 * | 3/2004 | Gupta | 514/2 |
| 2002/0169114 A1 | 11/2002 | Gupta | |
| 2002/0188100 A1 | 12/2002 | Plamondon et al. | |

FOREIGN PATENT DOCUMENTS

| WO | WO 98/35691 A1 | 8/1998 |
|---|---|---|
| WO | WO 99/15183 A1 | 4/1999 |
| WO | WO 00/57887 A1 | 10/2000 |
| WO | WO 01/02424 A2 | 1/2001 |
| WO | WO 02/059130 A1 | 1/2002 |
| WO | WO 02/059131 A1 | 8/2002 |

OTHER PUBLICATIONS

Ciechanover, "The Ubiquitin–Proteasome Proteolytic Pathway," Cell, vol. 79, pp. 13–21 (Oct. 7, 1994).
Gennaro, "Remington: The Science and Practice of Pharmacy," 20$^{th}$ Edition, Chapter 42, pp. 802–803 (2000).
Kataoka et al., "Totally Synthetic Polymer Gels Responding to External Glucose Concentration: Their Preparation and Application to On–Off Regulations of Insulin Release," J. Am. Chem. Soc., 120:12694–12695 (1998).
Kibbe, "Handbook of Pharmaceutical Excipients," 3$^{rd}$ Edition, pp. 324–328 (2000).
Korcek et al., "Absolute Rate Constants for the Autoxidation of Organometallic Compounds, Part II. Benzylboranes and 1–Phenylethylboranes," J. Chem. Soc., Perkin Trans. II, pp. 242–248 (1972).
Richardson et al., "A Phase 2 Study of Bortezomib in Relapsed, Refractory Myeloma," N. Engl. J. Med., vol. 348, No. 26, pp. 2609–2617 (Jun. 2003).
Snyder et al., "Aryl Boronic Acids. II. Aryl Boronic Anhydrides and their Amine Complexes," J. Am. Chem. Soc., 80, pp. 3611–3615 (1958).
Stella et al., "Development of Parenteral Formulations of Experimental Cytoxic Agents. I. Rhizoxin (NSC–332598)," International Journal of Pharmaceutics, vol. 43, pp. 191–199 (1988).
Williams et al., "The Effects of Cooling Rate on Solid Phase Transitions and Associated Vial Breakage Occurring in Frozen Mannitol Solutions," Journal of Parenteral Science & Technology, vol. 40, No. 4, pp. 135–141 (Jul.–Aug. 1986).
Williams et al., "Vial Breakage by Frozen Mannitol Solutions: Correlation with Thermal Characteristics and Effect of Steroisomerism, Additives, and Vial Configuration," Journal of Parenteral Science & Technology, vol. 45, No. 2, pp. 94–100 (Mar.–Apr. 1991).

* cited by examiner

Primary Examiner—Elvis O. Price
Assistant Examiner—Michael C. Henry
(74) Attorney, Agent, or Firm—Leydig, Voit & Mayer, Ltd.

(57) ABSTRACT

The present invention provides stable compounds prepared from boronic acid and lyophilized compounds thereof of the formula (1):

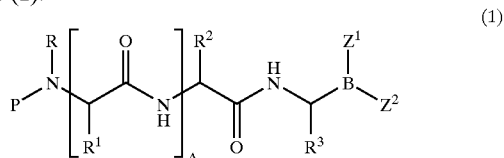

in which $Z^1$ and $Z^2$ are moieties derived from sugar. The invention also provides methods for preparing such compounds. Lyophilizing a mixture comprising a boronic acid compound and a moiety derived from sugar produces a stable composition that readily releases the boronic acid compound upon reconstitution in aqueous media.

105 Claims, No Drawings

FORMULATION OF BORONIC ACID COMPOUNDS

CROSS-REFERENCE TO RELATED APPLICATIONS

This patent application is a continuation of U.S. patent application Ser. No. 10/056,567, filed Jan. 25, 2002, now U.S. Pat. No. 6,713,446, and a continuation of U.S. patent application Ser. No. 10/056,563, filed Jan. 25, 2002, now U.S. Pat. No. 6,699,835, both of which claim the benefit of U.S. Provisional Patent Application No. 60/264,160, filed Jan. 25, 2001.

FIELD OF THE INVENTION

This invention relates to the formulation of pharmaceutical compounds. More particularly, the invention relates to stable, pharmaceutically acceptable compositions prepared from boronic acid compounds. The invention also relates to methods for preparing such compositions.

BACKGROUND OF THE INVENTION

Boronic acid and ester compounds display a variety of pharmaceutically useful biological activities. Shenvi et al., U.S. Pat. No. 4,499,082 (1985), discloses that peptide boronic acids are inhibitors of certain proteolytic enzymes. Kettner and Shenvi, U.S. Pat. No. 5,187,157 (1993); U.S. Pat. No. 5,242,904 (1993); and U.S. Pat. No. 5,250,720 (1993), describe a class of peptide boronic acids that inhibit trypsin-like proteases. Kleeman et al., U.S. Pat. No. 5,169,841 (1992), discloses N-terminally modified peptide boronic acids that inhibit the action of renin. Kinder et al., U.S. Pat. No. 5,106,948 (1992), discloses that certain tripeptide boronic acid compounds inhibit the growth of cancer cells.

Adams et al., U.S. Pat. No. 5,780,454 (1998), U.S. Pat. No. 6,066,730 (2000), U.S. Pat. No. 6,083,903 (2000), and U.S. Pat. No. 6,297,217 (2001), hereby incorporated by reference in their entirety, describe peptide boronic ester and acid compounds useful as proteasome inhibitors. The references also describe the use of boronic ester and acid compounds to reduce the rate of muscle protein degradation, to reduce the activity of NF-κB in a cell, to reduce the rate of degradation of p53 protein in a cell, to inhibit cyclin degradation in a cell, to inhibit the growth of a cancer cell, to inhibit antigen presentation in a cell, to inhibit NF-κB dependent cell adhesion, and to inhibit HIV replication. Brand et al., WO 98/35691, teaches that proteasome inhibitors, including boronic acid compounds, are useful for treating infarcts such as those that occur during stroke or myocardial infarction. Elliott et al., WO 99/15183, teaches that proteasome inhibitors are useful for treating inflammatory and autoimmune diseases.

Unfortunately, alkylboronic acids are relatively difficult to obtain in analytically pure form. Snyder et al., *J. Am. Chem. Soc.*, 3611 (1958), teaches that alkylboronic acid compounds readily form boroxines (anhydrides) under dehydrating conditions. Also, alkylboronic acids and their boroxines are often air-sensitive. Korcek et al., *J. Chem. Soc., Perkin Trans.* 2 242 (1972), teaches that butylboronic acid is readily oxidized by air to generate 1-butanol and boric acid. These difficulties limit the pharmaceutical utility of boronic acid compounds, complicating the characterization of pharmaceutical agents comprising boronic acid compounds and limiting their shelf life.

There is thus a need in the art for improved formulations of boronic acid compounds. Ideally, such formulations would be conveniently prepared, would exhibit enhanced stability and longer shelf life as compared to the free boronic acid compound, and would readily liberate the bioactive boronic acid compound when administered to a subject in need of boronic acid therapy.

SUMMARY OF THE INVENTION

The present invention provides stable, pharmaceutically acceptable compositions prepared from boronic acid compounds. The invention also provides methods for preparing such compositions. The invention provides the discovery that lyophilization of an aqueous mixture comprising a boronic acid compound and a compound having at least two hydroxyl groups produces a stable composition that readily releases the boronic acid compound upon dissolution in aqueous media.

In a first aspect, the invention provides compounds having formula (1):

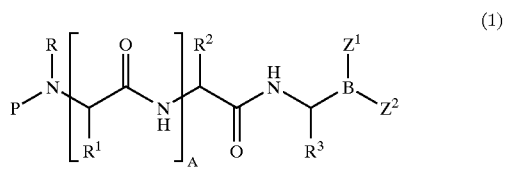

wherein:

P is hydrogen or an amino-group protecting moiety;

R is hydrogen or alkyl;

A is 0, 1, or 2;

$R^1$, $R^2$, and $R^3$ are independently hydrogen, alkyl, cycloalkyl, aryl, or —$CH_2$—$R^5$;

$R^5$, in each instance, is one of aryl, aralkyl, alkaryl, cycloalkyl, heterocyclyl, heteroaryl, or —W—$R^6$, where W is a chalcogen and $R^6$ is alkyl;

where the ring portion of any of said aryl, aralkyl, alkaryl, cycloalkyl, heterocyclyl, or heteroaryl in $R^1$, $R^2$, $R^3$ or $R^5$ can be optionally substituted; and $Z^1$ and $Z^2$ together form a moiety derived from a sugar, wherein the atom attached to boron in each case is an oxygen atom.

In a second aspect, the invention provides a composition comprising a compound of formula (2):

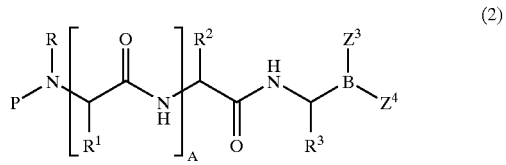

wherein:

P is hydrogen or an amino-group-protecting moiety;

R is hydrogen or alkyl;

A is 0, 1, or 2;

$R^1$, $R^2$, and $R^3$ are independently hydrogen, alkyl, cycloalkyl, aryl, or —$CH_2$—$R^5$;

$R^5$, in each instance, is one of aryl, aralkyl, alkaryl, cycloalkyl, heterocyclyl, heteroaryl, or —W—$R^6$, where W is a chalcogen and $R^6$ is alkyl;

where the ring portion of any of said aryl, aralkyl, alkaryl, cycloalkyl, heterocyclyl, or heteroaryl in $R^1$, $R^2$, $R^3$ or $R^5$ can be optionally substituted; and $Z^3$ and $Z^4$ together form a moiety derived from a compound having at least two hydroxyl groups separated by at least two connecting atoms in a chain or ring, said chain or ring comprising carbon atoms and, optionally, a heteroatom or heteroatoms which can be N, S, or O;

in a lyophilized powder.

In a third aspect, the invention provides a method for formulating a boronic acid compound, the method comprising:

(a) preparing a mixture comprising (i) water, (ii) a boronic acid compound; and (iii) a compound having at least two hydroxyl groups separated by at least two connecting atoms in a chain or ring, the chain or ring comprising carbon atoms, and optionally, a heteroatom or heteroatoms which can be N, S, or O; and (b) lyophilizing the mixture.

In a fourth aspect, the invention provides compositions prepared by the methods of the invention.

DESCRIPTION OF THE PREFERRED EMBODIMENTS

The invention provides stable, pharmaceutically acceptable compositions prepared from boronic acid compounds and methods for preparing the compositions. The invention also provides novel boronate ester compounds.

For purposes of the present invention, the following definitions will be used:

As used herein, the terms "formulate" and "formulation" refer to the preparation of a boronic acid compound in a form suitable for administration to a mammalian subject, preferably a human. Often, formulation of the boronic acid compound comprises addition of pharmaceutically acceptable excipients, diluents, or carriers. In some embodiments, formulation of the boronic acid compound comprises formation of a chemical derivative of the boronic acid compound, preferably formation of a boronate ester. The term "formulation" refers to any form commonly used for pharmaceutical administration, including solids, liquids, suspensions, creams, and gels. For purposes of the present invention, the formulation is preferably a lyophilized powder.

As used herein, the term "lyophilized powder" refers to any solid material obtained by lyophilization of an aqueous mixture.

By "stable formulation" is meant any formulation having sufficient stability to have utility as a pharmaceutical agent. Preferably, the formulation has sufficient stability to allow storage at a convenient temperature, preferably between 0° C. and 40° C., for a reasonable period of time, preferably longer than one month, more preferably longer than three months, even more preferably longer than six months, and most preferably longer than one year.

As employed herein, the term "boronic acid" refers to any chemical compound comprising a —B(OH), moiety. Snyder et al., *J. Am. Chem. Soc.* 3611 (1958), teaches that alkyl boronic acid compounds readily form oligomeric anhydrides by dehydration of the boronic acid moiety. Thus, unless otherwise apparent from context, the term "boronic acid" is expressly intended to encompass free boronic acids, oligomeric anhydrides, including, but not limited to, dimers, trimers, and tetramers, and mixtures thereof.

As employed herein, the term "compound having at least two hydroxyl groups" refers to any compound having two or more hydroxyl groups. For purposes of the present invention, the two hydroxyl groups are preferably separated by at least two connecting atoms, preferably from about 2 to about 5 connecting atoms, more preferably 2 or 3 connecting atoms. The connecting atoms may be in a chain or a ring, the chain or ring comprising carbon atoms and, optionally, a heteroatom or heteroatoms, which can be N, S, or O. For convenience, the term "dihydroxy compound" may be used to refer to a compound having at least two hydroxyl groups, as defined above. Thus, as employed herein, the term "dihydroxy compound" is not intended to be limited to compounds having only two hydroxyl groups.

As employed herein, the term "amino-group protecting moiety" refers to any group used to derivatize an amino group, especially an N-terminal amino group of a peptide or amino acid. Such groups include, without limitation, alkyl, acyl, alkoxycarbonyl, aminocarbonyl, and sulfonyl moieties. However, the term "amino-group protecting moiety" is not intended to be limited to those particular protecting groups that are commonly employed in organic synthesis, nor is it intended to be limited to groups that are readily cleavable.

The term "chalcogen" as employed herein refers to the elements oxygen or sulfur.

The term "alkyl" as employed herein refers to straight and branched chain aliphatic groups having from 1 to 12 carbon atoms, preferably 1–8 carbon atoms, more preferably 1–6 carbon atoms, and still more preferably 1–4 carbon atoms, which may be optionally substituted with one, two or three substituents. Unless otherwise explicitly stated, the term "alkyl" is meant to include saturated, unsaturated, and partially unsaturated aliphatic groups. When unsaturated groups are particularly intended, the terms "alkenyl" or "alkynyl" will be used. When only saturated groups are intended, the term "saturated ailcyl" will be used. Preferred saturated alkyl groups include, without limitation, methyl, ethyl, propyl, isopropyl, butyl, isobutyl, sec-butyl, tert-butyl, pentyl, and hexyl.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally may be optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

An "aryl" group is a $C_6$–$C_{14}$ aromatic moiety comprising one to three aromatic rings, which may be optionally substituted. Preferably, the aryl group is a $C_6$–$C_{10}$ aryl group. Preferred aryl groups include, without limitation, phenyl, naphthyl, anthracenyl, and fluorenyl. An "aralkyl" or "arylalkyl" group comprises an aryl group covalently linked to an alkyl group, either of which may independently be optionally substituted or unsubstituted. Preferably, the aralkyl group is ($C_1$–$C_6$)alk($C_6$–$C_{10}$)aryl, including, without limitation, benzyl, phenethyl, and naphthylmethyl. An "alkaryl" or "alkylaryl" group is an aryl group having one or more alkyl substituents. Examples of alkaryl groups include, without limitation, tolyl, xylyl, mesityl, ethylphenyl, tert-butylphenyl, and methylnaphthyl.

The terms "heterocycle," "heterocyclic," and "heterocyclyl" refer to any stable ring structure having from about 3 to about 8 atoms, wherein one or more atoms are selected from the group consisting of N, O, and S. The nitrogen and sulfur heteroatoms of the heterocyclic moiety may be optionally oxidized, and the nitrogen atoms may be optionally quaternized. The heterocyclic ring can be attached to its pendant group at any heteroatom or carbon atom that results in a stable formula. The term "stable compound" or "stable formula" is meant to refer to a compound that is sufficiently robust to survive isolation to a useful degree of purity from a reaction mixture and formulation into an efficacious therapeutic agent.

The heterocyclic group may be optionally substituted on carbon at one or more positions with any of the substituents recited above. The heterocyclic group may also independently be substituted on nitrogen with alkyl, aryl, aralkyl, alkylcarbonyl, alkylsulfonyl, arylcarbonyl, arylsulfonyl, alkoxycarbonyl, aralkoxycarbonyl, oxo, or hydroxy, or on sulfur with oxo or lower alkyl. Preferred heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholinyl. The heterocyclic group may also be fused to an aryl, heteroaryl, or heterocyclic group. Examples of such fused heterocycles include, without limitation, tetrahydroquinoline and dihydrobenzofuran.

As used herein, the terms "heteroaryl" and "aromatic heterocyle" refer to groups having 5- to 14-membered rings, preferably 5-, 6-, 9-, or 10-membered rings; having 6, 10, or 14 π electrons shared in a cyclic array; and having, in addition to carbon atoms, from one to about four, preferably from one to about three, heteroatoms selected from the group consisting of N, O, and S. The heteroaryl group may be optionally substituted on carbon at one or more positions with any of the substituents recited above. Preferred heteroaryl groups include, without limitation, thienyl, benzothienyl, furanyl, benzofuranyl, dibenzofuranyl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, and isoxazolyl.

As employed herein, a "substituted" alkyl, cycloalkyl, aryl, heterocyclyl, or heteroaryl group is one having from one and to about four, preferably from one to about three, more preferably one or two, non-hydrogen substituents. Suitable substituents include, without limitation, halo, hydroxy, oxo, nitro, haloalkyl, alkyl, alkaryl, aryl, aralkyl, alkoxy, aryloxy, amino, acylamino, alkylcarbamoyl, arylcarbamoyl, aminoalkyl, alkoxycarbonyl, carboxy, hydroxyalkyl, alkylsulfonyl, arenesulfonyl, alkylsulfonamido, arenesulfonamido, aralkylsulfonamido, alkylcarbonyl, acyloxy, cyano, and ureido groups. Preferably the substituents are independently selected from the group consisting of $C_1$–$C_6$ alkyl, $C_3$–$C_8$ cycloalkyl, ($C_1$–$C_6$) alkyl($C_3$–$C_8$)cycloalkyl, $C_2$–$C_8$ alkenyl, $C_2$–$C_8$ alkynyl, cyano, amino, $C_1$–$C_6$ alkylamino, di($C_1$–$C_6$)alkylamino, benzylamino, dibenzylamino, nitro, carboxy, carbo($C_1$–$C_6$) alkoxy, trifluoromethyl, halogen, $C_1$–$C_6$ alkoxy, $C_6$–$C_{10}$ aryl, ($C_6$–$C_{10}$)aryl($C_1$–$C_6$)alkyl, ($C_6$–$C_{10}$)aryl($C_1$–$C_6$) alkoxy, hydroxy, $C_1$–$C_6$ alkylthio, $C_1$–$C_6$ alkylsulfinyl, $C_1$–$C_6$ alkylsulfonyl, $C_6$–$C_{10}$ arylthio, $C_6$–$C_{10}$ arylsulfinyl, $C_6$–$C_{10}$ arylsulfonyl, $C_6$–$C_{10}$ aryl, ($C_1$–$C_6$)alkyl($C_6$–$C_{10}$) aryl, and halo($C_6$–$C_{10}$)aryl.

The term "halogen" or "halo" as employed herein refers to chlorine, bromine, fluorine, or iodine.

The term oxo refers to an oxygen atom, which forms a carbonyl when attached to carbon, an N-oxide when attached to nitrogen, and a sulfoxide or sulfone when attached to sulfur.

As herein employed, the term "acyl" refers to an alkylcarbonyl or arylcarbonyl substituent.

The term "acylamino" refers to an amide group attached at the nitrogen atom. The term "carbamoyl" refers to an amide group attached at the carbonyl carbon atom. The nitrogen atom of an acylamino or carbamoyl substituent may be additionally substituted. The term "sulfonamido" refers to a sulfonamide substituent attached by either the sulfur or the nitrogen atom. The term "amino" is meant to include $NH_2$, alkylamino, arylamino, and cyclic amino groups.

The term "ureido" as employed herein refers to a substituted or unsubstituted urea moiety.

In a first aspect, the invention provides compounds having formula (1):

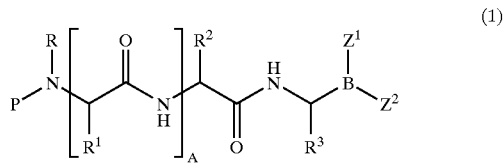

wherein

P is hydrogen or an amino-group protecting moiety;

R is hydrogen or alkyl;

A is 0, 1, or 2;

$R^1$, $R^2$, and $R^3$ are independently hydrogen, alkyl, cycloalkyl, aryl, or —$CH_2$—$R^5$;

$R^5$, in each instance, is one of aryl, aralkyl, alkaryl, cycloalkyl, heterocyclyl, heteroaryl, or —W—$R^6$, where W is a chalcogen and $R^6$ is alkyl;

where the ring portion of any of said aryl, aralkyl, alkaryl, cycloalkyl, heterocyclyl, or heteroaryl in $R^1$, $R^2$, $R^3$ or $R^5$ can be optionally substituted; and $Z^1$ and $Z^2$ together form a moiety derived from a sugar, wherein the atom attached to boron in each case is an oxygen atom.

As used herein, the term "moiety derived from a sugar" refers to a moiety formed by removing the hydrogen atoms from two hydroxyl groups of any sugar moiety. The moiety derived from a sugar may be attached to boron by any two of the hydroxyl groups of the sugar. For example, in various embodiments, the boronate ester forms a 5-, 6-, 7-, 8-, or 9-membered ring. In some preferred embodiments, the boronate ester forms a 5- or 6-membered ring.

The sugar is preferably a monosaccharide or disaccharide. Non-limiting examples of suitable sugars include, glucose, sucrose, fructose, trehalose, xylitol, mannitol, and sorbitol. In certain preferred embodiments, the sugar is a reduced sugar, more preferably mannitol or sorbitol. Thus, in the embodiment wherein the sugar is mannitol or sorbitol, $Z^1$ and $Z^2$ of the compound of formula (1) together form a moiety of formula $C_6H_{12}O_6$, wherein the oxygen atoms of the two deprotonated hydroxyl groups form covalent attachments with boron to form a boronate ester compound.

Preferably, the mannitol or sorbitol boronate ester compound has one of the following structures:

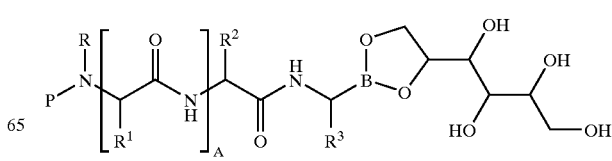

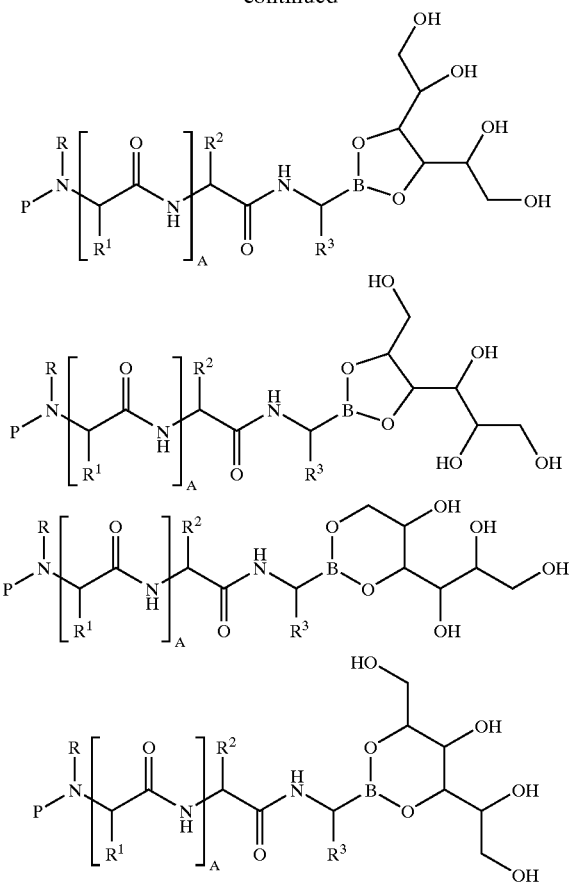

However, structures with larger boronate ester ring sizes are also possible.

In certain preferred embodiments, the mannitol or sorbitol boronate ester forms a symmetrical 5-membered ring having the following structure:

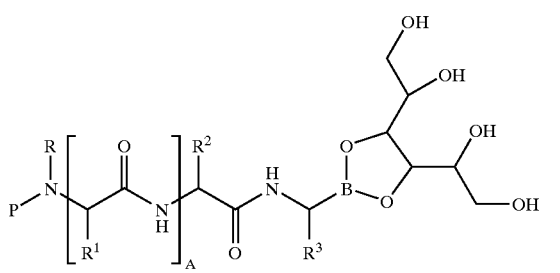

Preferably, the mannitol or sorbitol is of the D-configuration, although the L-configuration may also be used. In certain particularly preferred embodiments, $Z^1$ and $Z^2$ together form a moiety derived from D-mannitol. In these embodiments, the boronate ester compound preferably has one of the following structures:

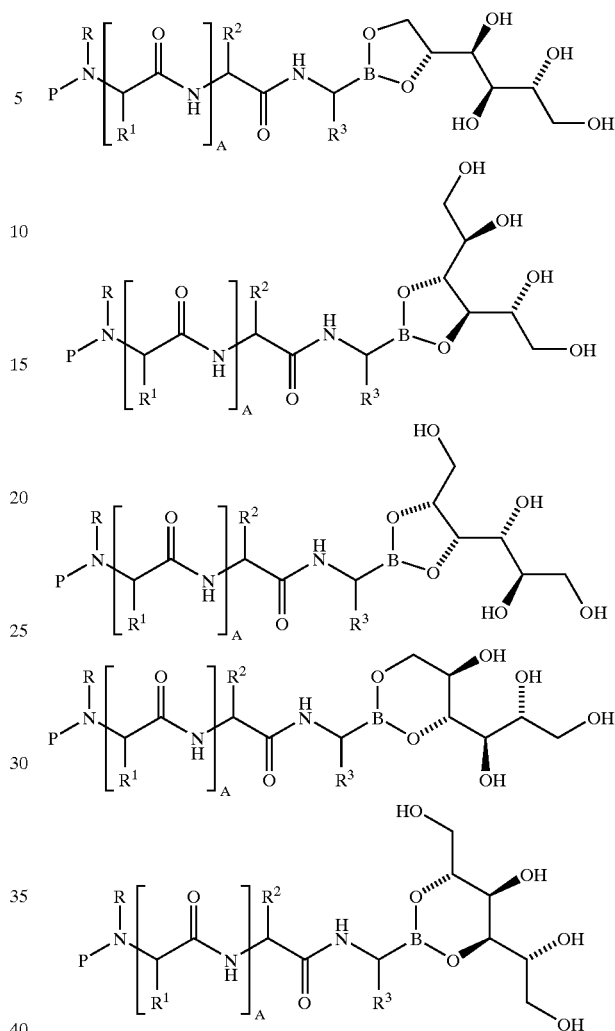

However, structures with larger boronate ester ring sizes are also possible.

In certain particularly preferred embodiments, the boronate ester compound has the following structure:

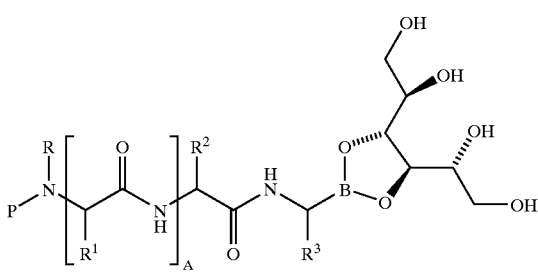

The P moiety of the compound of formula (1) is preferably hydrogen or one of $R^7$—C(O)—, $R^7$—S(O)$_2$—, $R^7$—NH—C(O)—, or $R^7$—O—C(O)—, where $R^7$ is one of alkyl, aryl, alkaryl, or aralkyl, any of which can be optionally substituted, or when P is $R^7$—C(O)— or $R^7$—S(O)$_2$—, $R^7$ can also be an optionally substituted 5- to 10-membered saturated, partially unsaturated, or aromatic heterocycle.

In certain preferred embodiments, P is one of $R^7$—C(O)— or $R^7$—S(O)$_2$—, and $R^7$ is an optionally substituted 5- to 10-membered saturated, partially unsaturated, or aromatic heterocycle. Preferably, $R^7$ is an aromatic heterocycle, more preferably pyrazinyl, pyridyl, quinolyl, or quinoxalinyl, or a saturated heterocycle, preferably morpholinyl. In some preferred embodiments, P is (2-pyrazine) carbonyl or (2-pyrazine)sulfonyl.

In some preferred embodiments, R is hydrogen. In some other preferred embodiments, R is alkyl, preferably $C_1$–$C_6$, alkyl, more preferably $C_1$–$C_4$, alkyl, and most preferably methyl or ethyl.

The variable A in formula (1) can be 0, 1, or 2. Thus, when A is zero, the residue within the brackets is not present and the boronate ester compound is a dipeptide. Similarly, where A is 1, the residue within the brackets is present and the compound is a tripeptide. Where A is 2, the compound is a tetrapeptide. In certain particularly preferred embodiments, A is zero. For purposes of the invention, the terms "peptide," 'dipeptide," and "tripeptide" are intended to encompass compounds comprising natural amino acid residues, unnatural amino acid residues, or a combination of natural and unnatural amino acid residues. It will be apparent from formulae (1)–(3), that the terms "peptide," "dipeptide," and "tripeptide" are used herein to refer to compounds in which the carboxylic acid functionality of the C-terminal amino acid residue is replaced by a boronic acid or boronate ester functionality.

It is preferred that the substituents $R^1$, $R^2$, and $R^3$ in formula (1) are each independently one of hydrogen, $C_1$–$C_8$, alkyl, $C_3$–$C_{10}$ cycloalkyl, or $C_6$–$C_{10}$ aryl, or —$CH_2$—$R^5$, wherein each of $R^1$, $R^2$, $R^3$, and $R^5$ may be optionally substituted. More preferably, $R^1$, $R^2$, and $R^3$ are each independently one of $C_1$–$C_4$ alkyl or —$CH_2$—$R^5$, and $R^5$ is one of cycloalkyl, aryl, heterocyclyl, heteroaryl, or —W—$R^6$ where W is chalcogen and $R^6$ is alkyl. Preferably, $R^5$ is one of $C_6$–$C_{10}$ aryl, ($C_6$–$C_{10}$)ar($C_1$–$C_6$)alkyl, ($C_1$–$C_6$)alk($C_6$–$C_{10}$)aryl, $C_3$–$C_{10}$ cycloalkyl, $C_1$–$C_8$ alkoxy, or $C_1$–$C_8$, alkylthio or a 5- to 10-membered heteroaryl ring.

In certain particularly preferred embodiments, the compound of formula (1) is one of:

D-Mannitol N-(2-pyrazine)carbonyl-L-phenylalanine-L-leucine boronate (also known as D-Mannitol [(1R)-3-methyl-1-[[(2S)-1-oxo-3-phenyl-2-[(pyrazinylcarbonyl)amino]propyl]amino]butyl]boronate);

D-Mannitol N-(2-quinoline)sulfonyl-L-homophenylalanine-L-leucine boronate;

D-Mannitol N-(3-pyridine)carbonyl-L-phenylalanine-L-leucine boronate;

D-Mannitol N-(4-morpholine)carbonyl-L-phenylalanine-L-leucine boronate;

D-Mannitol N-(4-morpholine)carbonyl-β-(1-naphthyl)-L-alanine-L-leucine boronate;

D-Mannitol N-(8-quinoline)sulfonyl-β-(1-naphthyl)-L-alanine-L-leucine boronate;

D-Mannitol N-(4-morpholine)carbonyl-(O-benzyl)-L-tyrosine-L-leucine boronate;

D-Mannitol N-(4-morpholine)carbonyl-L-tyrosine-L-leucine boronate; or

D-Mannitol-N-(4-morpholine)carbonyl-[O-(2-pyridylmethyl)]-L-tyrosine-L-leucine boronate.

In a second aspect, the invention provides a composition comprising a compound of formula (2):

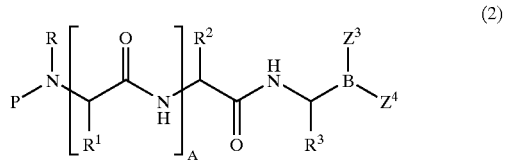

wherein:

P is hydrogen or an amino-group protecting moiety;

R is hydrogen or alkyl;

A is 0, 1, or 2;

$R^1$, $R^2$, and $R^3$ are independently hydrogen, alkyl, cycloalkyl, aryl, or —$CH_2$—$R^5$;

$R^5$, in each instance, is one of aryl, aralkyl, alkaryl, cycloalkyl, heterocyclyl, heteroaryl, or —W—$R^6$, where W is a chalcogen and $R^6$ is alkyl;

where the ring portion of any of said aryl, aralkyl, alkaryl, cycloalkyl, heterocyclyl, or heteroaryl in $R^1$, $R^2$, $R^3$ or $R^5$ can be optionally substituted; and $Z^3$ and $Z^4$ together form a moiety derived from a compound having at least two hydroxyl groups separated by at least two connecting atoms in a chain or ring, said chain or ring comprising carbon atoms and, optionally, a heteroatom or heteroatoms which can be N, S, or O; in a lyophilized powder.

Preferred values for the variables P, R, A, $R^1$, $R^2$, $R^3$, $R^5$, and $R^6$ according to this aspect of the invention are as described above for the first aspect.

The term "moiety derived from a compound having at least two hydroxyl groups" according to this aspect of the invention is used analogously to the term "moiety derived from a sugar" described above, and thus refers to a moiety formed by removing the hydrogen atoms from two hydroxyl groups of a compound having at least two hydroxyl groups. The moiety derived from a compound having at least two hydroxyl groups may be attached to boron by the oxygen atoms of any two of its hydroxyl groups. Preferably, the boron atom, the oxygen atoms attached to boron, and the atoms connecting the two oxygen atoms together form a 5- or 6-membered ring. Examples of suitable compounds having at least two hydroxyl groups ("dihydroxy compounds") include, without limitation, pinanediol, pinacol, perfluoropinacol, ethylene glycol, diethylene glycol, catechol, 1,2-cyclohexanediol, 1,3-propanediol, 2,3-butanediol, 1,2-butanediol, 1,4-butanediol, glycerol, and diethanolamine.

For purposes of the present invention, the dihydroxy compound is preferably pharmaceutically acceptable and is preferably miscible or soluble in water or an alcoholic solvent. In some preferred embodiments, the dihydroxy compound is a sugar, as described above, preferably a monosaccharide or disaccharide, more preferably a reduced sugar, and most preferably sorbitol or mannitol. In certain particularly preferred embodiments, the dihydroxy compound is mannitol, most preferably D-mannitol.

The composition according to this aspect of the invention is in the form of a lyophilized powder. In some preferred embodiments, the composition also comprises the free dihydroxy compound. Preferably, the dihydroxy compound and the compound of formula (1) are present in the mixture in a molar ratio ranging from about 0.5:1 to about 100:1, more preferably from about 5:1 to about 100:1. In some embodiments, the dihydroxy compound and the compound of formula (1) are present in a ratio ranging from about 10:1 to about 100:1.

In some preferred embodiments, the composition further comprises one or more other pharmaceutically acceptable excipients, carriers, diluents, fillers, salts, buffers, stabilizers, solubilizers, and other materials well known in the art. The preparation of pharmaceutically acceptable formulations containing these materials is described in, e.g., *Remington's Pharmaceutical Sciences*, 18th Edition, ed. A. Gennaro, Mack Publishing Co., Easton, Pa., 1990.

The compounds and compositions according to the first and second aspects of the invention may be prepared by the methods described herein, or by any method suitable to produce the compound or composition. For example, the boronate esters of formula (1) can be prepared from the corresponding boronic acids by lyophilization in the presence of mannitol or sorbitol, as described herein, or, alternatively, can be prepared from another boronate ester by transesterification. Alternatively, the boronate esters of formula (1) can be prepared by incorporation of the sugar moiety at an earlier stage in the synthesis.

In a third aspect, the invention provides a method for formulating a boronic acid compound, the method comprising:

(a) preparing a mixture comprising
  (i) water,
  (ii) a boronic acid compound; and
  (iii) a compound having at least two hydroxyl groups separated by at least two connecting atoms in a chain or ring, the chain or ring comprising carbon atoms, and optionally, a heteroatom or heteroatoms which can be N, S, or O; and
(b) lyophilizing the mixture.

In certain preferred embodiments, the mixture comprises one or more co-solvents in addition to water. Preferably, the co-solvent is miscible with water. More preferably, the co-solvent is an alcohol, including, without limitation, ethanol and tert-butanol. The composition of the solvent mixture may range from about 5% to about 95% v/v alcohol. In some embodiments, the aqueous solvent mixture comprises from about 30% to about 50% alcohol, preferably from about 35% to about 45% alcohol. In certain preferred embodiments, the aqueous solvent mixture comprises about 40% tert-butanol.

In some other embodiments, the aqueous solvent mixture comprises from about 1% to about 15% alcohol, preferably from about 5% to about 10% alcohol. In certain preferred embodiments, the aqueous solvent mixture comprises from about 5% to about 10% ethanol.

Preferably, the compound having at least two hydroxyl groups and the boronic acid compound are present in the mixture in a w/w ratio ranging from about 1:1 to about 100:1. In various embodiments, the w/w ratio of dihydroxy compound to boronic acid compound is about 10:1, 20:1, 30:1, 40:1, 50:1, 60:1, 70:1, 80:1, 90:1, or 100:1. Other ratios are also possible.

The aqueous mixture can be prepared by any order of addition. For example, in some embodiments, the dihydroxy compound is added to an aqueous mixture comprising a boronic acid compound. In some other embodiments, the boronic acid compound is added to an aqueous mixture comprising a dihydroxy compound. In still yet other embodiments, the boronic acid compound and dihydroxy compound can be added at the same time, or nearly at the same time. In some embodiments, it may be advantageous initially to add the boronic acid compound and/or the dihydroxy compound to a solvent mixture containing a higher percentage of co-solvent than is desired for the lyophilization step, and then dilute with water.

In some preferred embodiments, the mixture further comprises one or more pharmaceutically acceptable excipients, carriers, diluents, fillers, salts, buffers, stabilizers, solubilizers, and other materials well known in the art. The preparation of pharmaceutically acceptable formulations containing these materials is described in, e.g., *Remington's Pharmaceutical Sciences*, 18th Edition, ed. A. Gennaro, Mack Publishing Co., Easton, Pa., 1990.

Preferred compounds having at least two hydroxyl groups ("dihydroxy compounds") according to this aspect of the invention are as described above for the second aspect.

In certain preferred embodiments, the boronic acid compound according to this aspect of the invention has formula (3):

$$\text{(3)}$$

$$P-N(R)-CH(R^1)-C(O)-N(H)-CH(R^2)-C(O)-N(H)-CH(R^3)-B(Z^5)(Z^6)$$

(with subscript A on the middle carbonyl group)

wherein:

P is hydrogen or an amino-group protecting moiety;

R is hydrogen or alkyl;

A is 0, 1, or 2;

$R^1$, $R^2$, and $R^3$ are independently hydrogen, alkyl, cycloalkyl, aryl, or —$CH_2$—$R^5$;

$R^5$, in each instance, is one of aryl, aralkyl, alkaryl, cycloalkyl, heterocyclyl, heteroaryl, or —W—$R^6$, where W is a chalcogen and $R^6$ is alkyl;

where the ring portion of any of said aryl, aralkyl, alkaryl, cycloalkyl, heterocyclyl, or heteroaryl in $R^1$, $R^2$, $R^3$ or $R^5$ can be optionally substituted; and $Z^5$ and $Z^6$ are each OH.

Preferred values for the variables P, R, A, $R^1$, $R^2$, $R^3$, $R^5$, and $R^6$ according to this aspect of the invention are as described above for the first aspect.

In certain particularly preferred embodiments, the boronic acid compound is one of:

N-(2-pyrazine)carbonyl-L-phenylalanine-L-leucine boronic acid;

N-(2-quinoline)sulfonyl-L-homophenylalanine-L-leucine boronic acid;

N-(3-pyridine)carbonyl-L-phenylalanine-L-leucine boronic acid;

N-(4-morpholine)carbonyl-L-phenylalanine-L-leucine boronic acid;

N-(4-morpholine)carbonyl-β-(1-naphthyl)-L-alanine-L-leucine boronic acid;

N-(8-quinoline)sulfonyl-β-(1-naphthyl)-L-alanine-L-leucine boronic acid;

N-(4-morpholine)carbonyl-(O-benzyl)-L-tyrosine-L-leucine boronic acid;

N-(4-morpholine)carbonyl-L-tyrosine-L-leucine boronic acid; or

N-(4-morpholine)carbonyl-[O-(2-pyridylmethyl)]-L-tyrosine-L-leucine boronic acid.

In a fourth aspect, the invention provides compositions prepared according to the methods according to the third aspect of the invention. In some preferred embodiments, formulation of a boronic acid according to the methods of the invention results in formation of a chemical derivative of the boronic acid compound, preferably formation of a boronate ester. In these embodiments, formulation of a boronic acid compound according to the method of the invention produces a composition comprising a boronate ester compound, according to the second aspect of the invention.

In some other embodiments, formulation of a boronic acid compound according to the method of the invention does not result in formation of a chemical derivative of the boronic acid compound. In these embodiments, the composition according to the third aspect of the invention comprises a boronic acid compound and a compound having at least two hydroxyl groups in a lyophilized powder.

The compositions according to the second and fourth aspects of the invention can be readily reconstituted by adding an aqueous solvent. Preferably, the reconstitution solvent is suitable for pharmaceutical administration. Examples of suitable reconstitution solvents include, without limitation, water, saline, and phosphate buffered saline (PBS). For clinical use, the compositions according to the second aspect of the invention are preferably reconstituted with sterile saline (0.9% w/v).

Upon reconstitution in aqueous medium, an equilibrium is established between any boronate ester present in the composition and the corresponding boronic acid. Typically, equilibrium is reached quickly, e.g., within 10–15 minutes, after the addition of water. The relative concentrations of boronate ester and boronic acid present at equilibrium is dependent upon the pH of the solution, temperature, and the ratio of dihydroxy compound to boronic acid compound.

The following examples are intended to further illustrate certain preferred embodiments of the invention, and are not intended to limit the scope of the invention.

EXAMPLES

Example 1

Preparation of a Lyophilized Formulation of N-(2-pyrazine)carbonyl-L-phenylalanine-L-leucine boronic acid with D-mannitol Approximately 40 mg of N-(2-pyrazine)carbonyl-L-phenylalanine-L-leucine boronic acid was weighed into a container, and 16 mL of tert-butanol was added. The container was closed and the suspension was warmed to approximately 45° C. for 5 minutes to complete dissolution of the compound. Water (24 mL) was added with stirring, followed by 0.4 g of mannitol, added as an excipient, 1% w/v. The mixture was stirred to complete dissolution and then cooled to ambient temperature. The solution was filtered through a 0.45 μm nylon membrane. One milliliter aliquots were placed in 5 mL serum bottles. Split rubber stoppers were partially inserted into the bottles, and the bottles were placed in a freeze dryer with a shelf temperature of −45° C. After approximately 1 hour, the vacuum was applied. The shelf temperature was allowed to rise gradually to −35° C. and maintained at −35° C. until the ice was gone from the samples (approximately 40 hours). The shelf temperature control was then turned off and the shelf temperature was allowed to gradually rise to 0° C. A secondary drying cycle was carried out by increasing the shelf temperature in 3 increments to 25° C. over a time period of 1.5 hours. The shelf temperature was maintained at 25° C. for 2 hours. The samples were sealed under nitrogen and removed from the freeze dryer.

The residual moisture content of the samples was determined by Karl Fischer analysis, using three lyophilized products. The water content was 0.88% by weight.

Fast Atom Bombardment (FAB) mass spectral analysis of the lyophilized product showed a strong signal at m/z=531, indicative of formation of a covalent boronate ester adduct between N-(2-pyrazine)carbonyl-L-phenylalanine-L-leucine boronic acid and D-mannitol. Glycerol was employed as the matrix, and a signal for the glycerol adduct with N-(2-pyrazine)carbonyl-L-phenylalanine-L-leucine boronic acid was observed at m/z=441. However, the intensity of the signal at m/z=441 was very low compared to the signal at m/z=531, possibly indicative of the enhanced stability of the D-mannitol adduct.

Example 2

Production-scale Preparation of a Lyophilized Formulation of N-(2-pyrazine)carbonyl-L-phenylalanine-L-leucine boronic acid with D-mannitol In a clean compounding vessel, a solution of 97% tert-butanol/3% Water for Injection was prepared by warming the required amount of tert-butanol to 35° C. and adding Water for Injection. Approximately 5% of the solution was reserved for use in rinsing. The solution was cooled to 15–30° C., and N-(2-pyrazine)carbonyl-L-phenylalanine-L-leucine boronic acid was added with stirring. The container was rinsed with the reserved tert-butanol/water solution, and the rinses were added to the main vessel. The mixture was stirred until the boronic acid compound was completely dissolved. Mannitol was added, with residual mannitol being rinsed into the reaction vessel with fresh Water for Injection. Sufficient Water for Injection was added to reduce the total alcohol content to 40% v/v. The mixture was stirred until the mannitol was completely dissolved. The mixture was filtered through a 0.22 micron filter. Aliquots of the filtered solution were placed into previously sterilized vials. The vials were sealed with lyophilization stoppers and were placed on lyophilizer chamber shelves maintained at −45° C. After two hours, the freeze dryer chamber was evacuated and the chamber pressure was adjusted to 100–200 microns with sterile nitrogen. The lyophilizer chamber shelves were warmed to −30° C. using an appropriate ramp rate, and held at that temperature for 10–15 hours. After each of the product thermocouples read −33° C. or warmer, the shelf temperature was adjusted to −15° C. over 7 hours using an appropriate ramp rate and maintained at that temperature for 5 hours. After all product thermocouples recorded the shelf temperature, the shelf was warmed to 0° C. over a period of at least 7 hours using an appropriate ramp rate. When all thermocouples recorded 0° C., the shelf was warmed to 27° C. and maintained at that temperature for 4 hours. At the end of the terminal drying phase, the chamber pressure was restored using sterile nitrogen, and the vials were sealed and removed.

Example 3

Reconstitution of N-(2-pyrazine)carbonyl-L-phenylalanine-L-leucine boronic acid

The lyophilized formulation of N-(2-pyrazine)carbonyl-L-phenylalanine-L-leucine boronic acid with D-mannitol was prepared as described in Example 1. One sample was reconstituted with 2 mL of water. Dissolution was complete within 1–2 minutes of shaking. The entire solution was transferred to a volumetric flask, diluted, and analyzed by HPLC for content of N-(2-pyrazine)carbonyl-L-phenylalanine-L-leucine boronic acid. The total drug content was 1.09 mg. A second sample was reconstituted with 1 mL of propylene glycol:EtOH:H$_2$O, 40:10:50. Dissolution was complete with 1 minute of shaking. The total drug content was 1.11 mg.

The lyophilized formulation was also reconstituted with 0.9% w/v saline. The lyophilized material dissolved readily at concentrations up to 6 mg/mL. By contrast, solid N-(2-pyrazine)carbonyl-L-phenylalanine-L-leucine boronic acid was not soluble in 0.9% w/v saline at a concentration of 1 mg/mL.

To be certain that free N-(2-pyrazine)carbonyl-L-phenylalanine-L-leucine boronic acid was rapidly liberated upon reconstitution of the lyophilized formulation in aqueous solution, the lyophilized formulation was dissolved in neat DMSO and assayed for inhibition of the chymotrypsin-like activity of the 20S proteasome as described in U.S. Pat. No. 5,780,454. Proteasome inhibition can only be observed if hydrolysis under the assay conditions is fast. The observed K$_i$ value of 0.3 nM is equivalent to that observed for free N-(2-pyrazine)carbonyl-L-phenylalanine-L-leucine boronic acid, indicating complete and rapid hydrolysis of the D-mannitol adduct under the assay conditions.

Example 4

HPLC Analysis of N-(2-pyrazine)carbonyl-L-phenylalanine-L-leucine boronic acid

System Parameters:

| | |
|---|---|
| Column: | Adsorbosphere-HS-C18, 5μ, 250 × 4.6 mm |
| Mobile Phase: | 65/35: methanol/water containing 0.1% TFA |
| Flow Rate: | 1.0 mL/min |
| Detection/Sensitivity: | PDA and UV at 255 nm, 0.1 aufs |
| Injection volume: | 25 μL |
| Internal Standard Solution: | 0.18 mg/mL diphenylamine in methanol |
| Sample Preparation: | Accurately weighed 0.5–1.5 mg portions of the sample or reference standard were dissolved in 2.00 mL of the internal standard solution. |

Chromatographic Parameters:

| | Sample | Internal Standard |
|---|---|---|
| Retention time | 8.4 min | 18.9 min |
| Capacity factor, k' | 2.0 | 5.8 |
| Asymmetry (10%) | 1.7 | 1.3 |
| Rel. Retention, α | | 0.34 |
| Resolution, R$_s$ = ΔT/ΣW$_{1/2}$ | | 15.1 |

ΔT and ΣW$_{1/2}$ are, respectively, the differences in retention times and the sum of the mid-width of the sample and internal standard peaks. Minor variation of the mobile phase is allowed to achieve results similar to those above.

Example 5

Stability of Formulations

Solid N-(2-pyrazine)carbonyl-L-phenylalanine-L-leucine boronic acid

N-(2-pyrazine)carbonyl-L-phenylalanine-L-leucine boronic acid was prepared as described in U.S. Pat. No. 5,780,454. The product was obtained as a white amorphous powder. The product was stable for more than 2 years when stored at −20° C., as determined by HPLC analysis (purity >97%). When stored at 2–8° C., the product was not stable for longer than 3–6 months.

Liquid N-(2-pyrazine)carbonyl-L-phenylalanine-L-leucine boronic acid

A sterile liquid formulation (0.5 mg/mL) of N-(2-pyrazine)carbonyl-L-phenylalanine-L-leucine boronic acid was prepared in 0.9% w/v saline, 2% v/v ethanol and 0.1% w/v ascorbic acid. When stored at 2–8° C., the liquid formulation was not stable for longer than 6 months, as determined by HPLC analysis.

Lyophilized D-mannitol N-(2-pyrazine)carbonyl-L-phenylalanine-L-leucine boronate The lyophilized product was prepared according to Example 1 and stored at 5° C., ambient temperature, 37° C., and 50° C. Stability was monitored for approximately 18 months by periodically reconstituting a sample and analyzing the entire contents of the bottle by HPLC. Over this time period, there was no loss of drug in the lyophilized product stored at any temperature and no evidence of degradation product peaks in the HPLC chromatograms.

Reconstituted Solution of N-(2-pyrazine)carbonyl-L-phenylalanine-L-leucine boronic acid The lyophilized product was prepared according to Example 1, and samples (2.5 mg/vial) were reconstituted with 2.5 mL of 0.9% w/v sterile saline. Dissolution was complete within 10 seconds and afforded a clear, colorless solution containing 1 mg/mL of N-(2-pyrazine)carbonyl-L-phenylalanine-L-leucine boronic acid. The solution showed no sign of degradation when stored at ambient temperature (23° C.) for 43 hours. No special care was taken to protect the solution from light.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar references in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A compound of the formula (1):

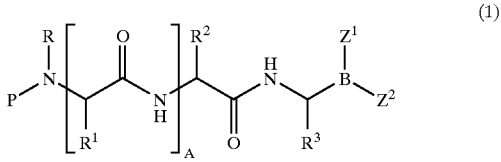

(1)

wherein
P is hydrogen or an amino-group protecting moiety;
R is hydrogen or alkyl;
A is 0, 1, or 2;
$R^1$, $R^2$, and $R^3$ are each independently hydrogen, alkyl, cycloalkyl, aryl, or —$CH_2$—$R^5$;
$R^5$, in each instance, is aryl, aralkyl, alkaryl, cycloalkyl, heterocyclyl, heteroaryl, or —W—$R^6$, where W is a chalcogen and $R^6$ is alkyl;
wherein the ring portion of any said aryl, aralkyl, alkaryl, cycloalkyl, heterocyclyl, or heteroaryl in $R^1$, $R^2$, $R^3$, or $R^5$ can be optionally substituted; and
$Z^1$ and $Z^2$ together form a moiety derived from a sugar, wherein the atom attached to boron in each case is an oxygen atom.

2. The compound of claim 1, wherein the sugar is a monosaccharide or disaccharide.

3. The compound of claim 1, wherein the sugar is a reduced sugar.

4. The compound of claim 3, wherein the reduced sugar is sorbitol.

5. The compound of claim 1, wherein A is 0.

6. The compound of claim 1, wherein P is $R^7$—C(O)—, $R^7$—$S(O)_2$—, $R^7$—NH—C(O)—, or $R^7$—O—C(O)—;
where $R^7$ is alkyl, aryl, alkaryl, or aralkyl, any of which can be optionally substituted, or when P is $R^7$—C(O)— or $R^7$—$S(O)_2$—, $R^7$ can also be an optionally substituted 5- to 10-membered saturated, partially saturated, or aromatic heterocycle.

7. The compound of claim 6, wherein P is $R^7$—C(O)— or $R^7$—$S(O)_2$—, and $R^7$ is an aromatic heterocycle.

8. The compound of claim 7, wherein P is (2-pyrazine)carbonyl or (2-pyrazine)sulfonyl.

9. The compound of claim 6, wherein
A is zero;
R is hydrogen or $C_1$–$C_8$ alkyl; and
$R^3$ is $C_1$–$C_6$ alkyl.

10. The compound of claim 9, wherein P is (2-pyrazine)sulfonyl.

11. The compound of claim 1, wherein
$R^1$, $R^2$, and $R^3$ are each independently hydrogen, $C_1$–$C_8$ alkyl, $C_3$–$C_{10}$ cycloalkyl, $C_6$–$C_{10}$ aryl, or —$CH_2$—$R^5$;
$R^5$ in each instance is $C_6$–$C_{10}$ aryl, ($C_6$–$C_{10}$)ar($C_1$–$C_6$) alkyl, ($C_1$–$C_6$)alk($C_6$–$C_{10}$)aryl, $C_3$–$C_{10}$ cycloalkyl, $C_1$–$C_8$ alkoxy, or $C_1$–$C_8$ alkylthio;
wherein the ring portion of any said aryl, aralkyl, alkaryl, cycloalkyl, heterocyclyl, or heteroaryl groups of $R^1$, $R^2$, $R^3$, or $R^5$ can be optionally substituted.

12. The compound of claim 1, wherein said compound is a sugar ester of:
N-(2-pyrazine)carbonyl-L-phenylalanine-L-leucine boronic acid;
N-(2-quinoline)sulfonyl-L-homophenylalanine-L-leucine boronic acid;
N-(3-pyridine)carbonyl-L-phenylalanine-L-leucine boronic acid;
N-(4-morpholine)carbonyl-L-phenylalanine-L-leucine boronic acid;
N-(4-morpholine)carbonyl-β-(1-naphthyl)-L-alanine-L-leucine boronic acid;
N-(8-quinoline)sulfonyl-β-(1-naphthyl)-L-alanine-L-leucine boronic acid;
N-(4-morpholine)carbonyl-(O-benzyl)-L-tyrosine-L-leucine boronic acid;
N-(4-morpholine)carbonyl-L-tyrosine-L-leucine boronic acid; or
N-(4-morpholine)carbonyl-[O-(2-pyridylmethyl)]-L-tyrosine-L-leucine boronic acid.

13. The compound of claim 1, wherein said compound is a sugar ester of N-(2-pyrazine)carbonyl-L-phenylalanine-L-leucine boronic acid.

14. A lyophilized compound of the formula (1):

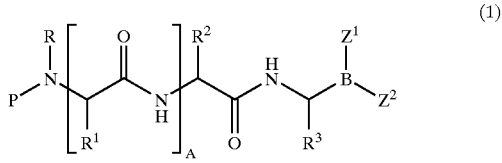

(1)

wherein
P is hydrogen or an amino-group protecting moiety;
R is hydrogen or alkyl;
A is 0, 1, or 2;
$R^1$, $R^2$, and $R^3$ are each independently hydrogen, alkyl, cycloalkyl, aryl, or —$CH_2$—$R^5$;
$R^5$, in each instance, is aryl, aralkyl, alkaryl, cycloalkyl, heterocyclyl, heteroaryl, or —W—$R^6$, where W is a chalcogen and $R^6$ is alkyl;
wherein the ring portion of any said aryl, aralkyl, alkaryl, cycloalkyl, hererocyclyl, or heteroaryl in $R^1$, $R^2$, $R^3$, or $R^5$ can be optionally substituted; and
$Z^1$ and $Z^2$ together form a moiety derived from a sugar, wherein the atom attached to boron in each case is an oxygen atom.

15. The compound of claim 14, wherein the sugar is a monosaccharide or disaccharide.

16. The compound of claim 14, wherein the sugar is a reduced sugar.

17. The compound of claim 14, wherein A is 0.

18. The compound of claim 16, wherein the reduced sugar is sorbitol.

19. The compound of claim 14, wherein P is $R^7$—C(O)—, $R^7$—$S(O)_2$—, $R^7$—NH—C(O)—, or $R^7$—O—C(O)—;
where $R^7$ is alkyl, aryl, alkaryl, or aralkyl, any of which can be optionally substituted, or when P is $R^7$—C(O)— or $R^7$—$S(O)_2$-, $R^7$ can also be an optionally substituted 5- to 10-membered saturated, partially saturated, or aromatic heterocycle.

20. The compound of claim 19, wherein P is $R^7$—C(O)— or $R^7$—$S(O)_2$—, and $R^7$ is an aromatic heterocycle.

21. The compound of claim 20, wherein P is (2-pyrazine)carbonyl or (2-pyrazine)sulfonyl.

22. The compound of claim 19, wherein
A is zero;
R is hydrogen or $C_1$–$C_8$ alkyl; and
$R^3$ is $C_1$–$C_6$ alkyl.

23. The compound of claim 22, wherein P is (2-pyrazine) sulfonyl.

24. The compound of claim 14, wherein
$R^1$, $R^2$, and $R^3$ are each independently hydrogen, $C_1$–$C_8$ alkyl, $C_3$–$C_{10}$ cycloalkyl, $C_6$–$C_{10}$ aryl, or —$CH_2$—$R^5$;
$R^5$ in each instance is $C_6$–$C_{10}$ aryl, ($C_6$–$C_{10}$)ar($C_1$–$C_6$)alkyl, ($C_1$–$C_6$)alk($C_6$–$C_{10}$)aryl, $C_3$–$C_{10}$ cycloalkyl, $C_1$–$C_8$ alkoxy, or $C_1$–$C_8$ alkylthio;
wherein the ring portion of any said aryl, aralkyl, alkaryl, cycloalkyl, heterocyclyl, or heteroaryl groups of $R^1$, $R^2$, $R^3$, or $R^5$ can be optionally substituted.

25. The compound of claim 20, wherein said compound is a sugar ester of:
N-(2-pyrazine)carbonyl-L-phenylalanine-L-leucine boronic acid;
N-(2-quinoline)sulfonyl-L-homophenylalanine-L-leucine boronic acid;
N-(3-pyridine)carbonyl-L-phenylalanine-L-leucine boronic acid;
N-(4-morpholine)carbonyl-L-phenylalanine-L-leucine boronic acid;
N-(4-morpholine)carbonyl-β-(1-naphthyl)-L-alanine-L-leucine boronic acid;
N-(8-quinoline)sulfonyl-β-(1-naphthyl)-L-alanine-L-leucine boronic acid;
N-(4-morpholine)carbonyl-(O-benzyl)-L-trosine-L-leucine boronic acid;
N-(4-morpholine)carbonyl-L-tyrosine-L-leucine boronic acid; or
N-(4-morpholine)carbonyl-[O-(2-pyridylmethyl)]-L-tyrosine-L-leucine boronic acid.

26. The lyophilized compound of claim 20, wherein said compound is a sugar ester of N-(2-pyrazine)carbonyl-L-phenylalanine-L-leucine boronic acid.

27. The compound of claim 14, wherein the compound is stable at 0° C. for at least one month.

28. The compound of claim 14, wherein the compound is stable at 40° C. for at least one month.

29. A method of preparing a lyophilized compound of the formula (1):

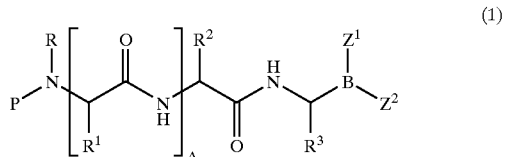

(1)

wherein
P is hydrogen or an amino-group protecting moiety;
R is hydrogen or alkyl;
A is 0, 1, or 2;
$R^1$, $R^2$, and $R^3$ are each independently hydrogen, alkyl, cycloalkyl, aryl, or —$CH_2$—$R^5$;
$R^5$ in each instance is aryl, aralkyl, alkaryl, cycloalkyl, heterocyclyl, heteroaryl, or —W—$R^6$, where W is a chalcogen and $R^6$ is alkyl;
wherein the ring portion of any said aryl, aralkyl, alkaryl, cycloalkyl, heterocyclyl, or heteroaryl in $R^1$, $R^2$, $R^3$, or $R^5$ can be optionally substituted; and $Z^1$ and $Z^2$ together form a moiety derived from a sugar;
the method comprising:
(a) preparing a mixture comprising
(i) water,
(ii) a compound of formula (3).

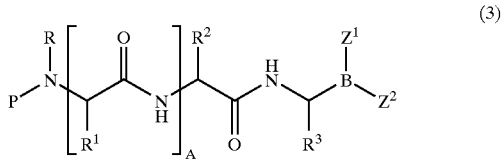

(3)

wherein P, R, A, $R^1$, $R^2$, and $R^3$ are as described above; and
Z' and Z" are OH; and
(iii) a sugar; and
(b) lyophilizing the mixture.

30. The method of claim 29, wherein the sugar is a monosaccharide or disaccharide.

31. The method of claim 29, wherein the sugar is a reduced sugar.

32. The method of claim 31, wherein the reduced sugar is sorbitol.

33. The method of claim 29, wherein P is $R^7$—C(O)—, $R^7$—S(O)$_2$—, $R^7$—NH—C(O)—, or $R^7$—O—C(O)—;
where $R^7$ is alkyl, aryl, alkaryl, or aralkyl, any of which can be optionally substituted, or when P is $R^7$—C(O)— or $R^7$—S(O)$_2$—, $R^7$ can also be an optionally substituted 5- to 10-membered saturated, partially saturated, or aromatic heterocycle.

34. The method of claim 33, wherein P is $R^7$—C(O)— or $R^7$—S(O)$_2$—, and $R^7$ is an aromatic heterocycle.

35. The method of claim 34, wherein P is (2-pyrazine)carbonyl or (2-pyrazine)sulfonyl.

36. The method of claim 29, wherein
A is zero;
R is hydrogen or $C_1$–$C_6$ alkyl; and
$R^3$ is $C_1$–$C_6$ alkyl.

37. The method of claim 36, wherein P is (2-pyrazine)sulfonyl.

38. The method of claim 29, wherein
$R^1$, $R^2$, and $R^3$ are each independently hydrogen, $C_1$–$C_8$ alkyl, $C_3$–$C_{10}$ cycloalkyl, $C_6$–$C_{10}$ aryl, or —$CH_2$—$R^5$;
$R^5$ in each instance is $C_6$–$C_{10}$ aryl, ($C_6$–$C_{10}$)ar($C_1$–$C_6$)alkyl, ($C_1$–$C_6$)alk($C_6$–$C_{10}$)aryl, $C_3$–$C_{10}$ cycloalkyl, $C_1$–$C_8$ alkoxy, or $C_1$–$C_8$ alkylthio;
wherein the ring portion of any said aryl, aralkyl, alkaryl, cycloalkyl, heterocyclyl, or heteroaryl groups of $R^1$, $R^2$, $R^3$, or $R^5$ can be optionally substituted.

39. The method of claim 29, wherein the compound of formula (3) is:
N-(2-pyrazine)carbonyl-L-phenylalanine-L-leucine boronic acid;
N-(2-quinoline)sulfonyl-L-homophenylalanine-L-leucine boronic acid;
N-(3-pyridine)carbonyl-L-phenylalanine-L-leucine boronic acid;
N-(4-morpholine)carbonyl-L-phenylalanine-L-leucine boronic acid;
N-(4-morpholine)carbonyl-β-(1-naphthyl)-L-alanine-L-leucine boronic acid;
N-(8-quinoline)sulfonyl-β-(1-naphthyl)-L-alanine-L-leucine boronic acid;
N-(4-morpholine)carbonyl-(O-benzyl)-L-tyrosine-L-leucine boronic acid;

N-(4-morpholine)carbonyl-L-tyrosine-L-leucine boronic acid; or

N-(4-morpholine)carbonyl-[O-(2-pyridylmethyl)]-L-tyrosine-L-leucine boronic acid.

40. The method of claim 39, wherein the compound of formula (3) is N-(2-pyrazine)carbonyl-L-phenylalanine-L-leucine boronic acid.

41. The method of claim 29, wherein the mixture further comprises a water-miscible solvent.

42. The method of claim 41, wherein the water-miscible solvent is an alcohol.

43. The method of claim 42, wherein the alcohol is tert-butanol.

44. The method of claim 29, wherein the sugar and the compound of formula (3) are present in at least a 1:1 raiio.

45. The method of claim 29, wherein the sugar and the compound of formula (3) are present in at least a 5:1 ratio.

46. A lyophilized cake comprising the compound of claim 14.

47. A composition comprising the compound of claim 1 and a pharmaceutically-acceptable carrier.

48. A composition comprising the compound of claim 6 and a pharmaceutically-acceptable carrier.

49. A composition compiising the compound of claim 10 and a pharmaceutically-acceptable carrier.

50. A composition comprising the compound of claim 13 and a pharmaceutically-acceptable carrier.

51. A composition comprising the compound of claim 14 and a pharmaceutically-acceptable carrier.

52. A composition comprising the compound of claim 19 and a pharmaceutically-acceptable carrier.

53. A composition comprising the compound of claim 23 and a pharmaceutically-acceptable carrier.

54. A composition comprising the compound of claim 26 and a pharmaceutically-acceptable carrier.

55. A lyophilized cake comprising the compound of claim 19.

56. A lyophilized cake comprising the compound of claim 23.

57. A lyophilized cake comprising the compound of claim 26.

58. The method of claim 37, wherein A is 0.

59. The method of claim 29 further comprising (c) reconstituting the lyophilized mixture with a pharmaceutically-acceptable carrier.

60. The method of claim 33 further comprising (c) reconstituting the lyophilized mixture with a pharmaceutically-acceptable carrier.

61. The method of claim 37 further comprising (c) reconstituting the lyophilized mixture with a pharmaceutically-acceptable carrier.

62. The method of claim 40 further comprising (c) reconstituting the lyophilized mixture with a pharmaceutically-acceptable carrier.

63. A composition comprising (i) the compound of formula (1) prepared in accordance with the method of claim 29 and (ii) a pharmaceutically-acceptable carrier.

64. A composition comprising (i) the compound of formula (1) prepared in accordance with the method of claim 33 and (ii) a pharmaceutically-acceptable carrier.

65. A composition comprising (i) the compound of formula (1) prepared in accordance with the method of claim 37 and (ii) a pharmaceutically-acceptable carrier.

66. A composition comprising (i) the compound of formula (1) prepared in accordance with the method of claim 40 and (ii) a pharmaceutically-acceptable carrier.

67. A lyophilized cake comprising the compound of formula (1) prepared in accordance with the method of claim 29.

68. A lyophilized cake comprising the compound of formula (1) prepared in accordance with the method of claim 33.

69. A lyophilized cake comprising the compound of formula (1) prepared in accordance with the method of claim 37.

70. A lyophilized cake comprising the compound of formula (1) prepared in accordance with the method of claim 40.

71. The compound of claim 9, wherein P is (2-pyrazine)carbonyl.

72. A composition comprising the compound of claim 71 and a pharmaceutically-acceptable carrier.

73. The compound of claim 22, wherein P is (2-pyrazine)carbonyl.

74. A composition comprising the compound of claim 73 and a pharmaceutically-acceptable carrier.

75. A lyophilized cake comprising the compound of claim 73.

76. The method of claim 36, wherein P is (2-pyrazine)carbonyl.

77. A composition comprising the compound of claim 76 and a pharmaceutically-acceptable carrier.

78. A lyophilized cake comprising the compound of formula (1) prepared in accordance with the method of claim 76.

79. The compound of claim 1, wherein P and R together form a cyclic moiety.

80. The compound of claim 79, wherein $Z^1$ and $Z^2$ together form a moiety derived from a monosaccharide or disaccharide.

81. The compound of claim 80, wherein

A is zero;

R is hydrogen or $C_1$–$C_8$ alkyl;

$R^3$ is $C_1$–$C_6$ alkyl; and

P is (2-pyrazine)carbonyl.

82. A composition comprising the compound of claim 79 and a pharmaceutically-acceptable carrier.

83. A composition comprising the compound of claim 80 and a pharmaceutically-acceptable carrier.

84. A composition comprising the compound of claim 81 and a pharmaceutically-acceptable carrier.

85. The compound of claim 14, wherein P and R together form a cyclic moiety.

86. The compound of claim 85, wherein $Z^1$ and $Z^2$ together form a moiety derived from a monosaccharide or disaccharide.

87. The compound of claim 86, wherein

A is zero;

R is hydrogen or $C_1$–$C_8$ alkyl;

$R^3$ is $C_1$–$C_6$ alkyl; and

P is (2-pyrazine)carbonyl.

88. A composition comprising the compound of claim 85 and a pharmaceutically-acceptable carrier.

89. A composition comprising the compound of claim 86 and a pharmaceutically-acceptable carrier.

90. A composition comprising the compound of claim 87 and a pharmaceutically-acceptable carrier.

91. A lyophilized cake comprising the compound of claim 85.

92. A lyophilized cake comprising the compound of claim 86.

93. A lyophilized cake comprising the compound of claim 87.

94. The method of claim 29, wherein P and R together form a cyclic moiety.

95. The method of claim 94, wherein $Z^1$ and $Z^2$ together form a moiety derived from a monosaccharide or disaccharide.

96. The method of claim 95, wherein

A is zero;

R is hydrogen or $C_1-C_8$ alkyl;

$R^3$ is $C_1-C_6$ alkyl; and

P is (2-pyrazine)carbonyl.

97. The method of claim 94 further comprising (c) reconstituting the lyophilized mixture with a pharmaceutically-acceptable carrier.

98. The method of claim 95 further comprising (c) reconstituting the lyophilized mixture with a pharmaceutically-acceptable carrier.

99. The method of claim 96 further comprising (c) reconstituting the lyophilized mixture with a pharmaceutically-acceptable carrier.

100. A composition comprising (i) the compound of formula (1) prepared in accordance with the method of claim 94 and (ii) a pharmaceutically-acceptable carrier.

101. A composition comprising (i) the compound of formula (1) prepared in accordance with the method of claim 95 and (ii) a pharmaceutically-acceptable carrier.

102. A composition comprising (i) the compound of formula (1) prepared in accordance with the method of claim 96 and (ii) a pharmaceutically-acceptable carrier.

103. A lyophilized cake comprising the compound of formula (1) prepared in accordance with the method of claim 94.

104. A lyophilized cake comprising the compound of formula (1) prepared in accordance with the method of claim 95.

105. A lyophilized cake comprising the compound of formula (1) prepared in accordance with the method of claim 96.

* * * * *

UNITED STATES PATENT AND TRADEMARK OFFICE
Certificate

Patent No. 6,958,319 B2                                                                 Patented: October 25, 2005

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Shanker Lal Gupta, Rockville, MD (US); Valentino J. Stella, Lawrence, KS (US); and Wanda Waugh, Lawrence, KS (US).

Signed and Sealed this Seventeenth Day of July 2012.

<div style="text-align: right;">
Shaojia Anna Jiang<br>
Supervisory Patent Examiner<br>
Art Unit 1623<br>
Technology Center 1600
</div>